(12) United States Patent
Tamion

(10) Patent No.: US 6,245,940 B1
(45) Date of Patent: Jun. 12, 2001

(54) METHOD OF MANUFACTURING AN ACID DERIVATIVE OF OSE BY DECARBOXYLATION WITH HYDROGEN PEROXIDE

(75) Inventor: Rodolphe Tamion, Allouagne (FR)

(73) Assignee: Roquette Freres, Lestrem (FR)

( * ) Notice: Subject to any disclaimer, the term of this patent is extended or adjusted under 35 U.S.C. 154(b) by 0 days.

(21) Appl. No.: 09/524,930

(22) Filed: Mar. 14, 2000

(30) Foreign Application Priority Data

Mar. 15, 1999 (FR) .................................................. 99 03158

(51) Int. Cl.$^7$ .................................................. C07C 51/00

(52) U.S. Cl. .......................................... 562/515; 562/587

(58) Field of Search .................................... 562/515, 485, 562/587

(56) References Cited

PUBLICATIONS

Liang, Yun Teh et al., vol.9(1), 1990, pp 75–84, XP000863175.
Humplett, Wilbert J., vol.4, 1967, pp 157–163, XP000863144.
Abstract of Japanese patent application n° 38–15610.
Isbell et al., 1974. Oxidation of sodium salts of alduronic and glyculosonic acids by sodium peroxide. Carbohydrate Research 36, 283–291.*

* cited by examiner

Primary Examiner—Paul J. Killos
Assistant Examiner—Mahreen Chaudhry
(74) Attorney, Agent, or Firm—Henderson & Sturm LLP

(57) ABSTRACT

The invention relates to a method of manufacturing an acid derivative of ose containing n carbon atoms on the carbonic chain, characterised by the fact that an acid derivative of ose with n+1 carbon atoms containing at least one α ketone function, and/or one of its salts, is brought into contact with hydrogen peroxide in a reaction medium without pH regulation.

20 Claims, No Drawings

METHOD OF MANUFACTURING AN ACID DERIVATIVE OF OSE BY DECARBOXYLATION WITH HYDROGEN PEROXIDE

The subject matter of the present invention is a method of manufacturing an acid derivative of ose.

More precisely, its subject matter is a method of manufacturing an acid derivative of ose containing n carbon atoms on the hydrocarbonic chain, from an acid derivative of ose with n+1 carbon atoms having at least one α ketone function, or one of its salts, said method consisting in bringing said acid derivative of ose with n+1 carbon atoms into contact with hydrogen peroxide in a reaction medium without pH regulation.

In the sense of the invention, the terms are agreed to mean the following:

"acid derivative of ose containing at least one α ketone function": a mono- or dicarboxylic acid derivative of an aldose, containing a ketone function in α of the acid function or functions, "aldose": an ose containing one aldehyde function, in particular a pentose or a hexose containing such a function, preferably chosen among xylose, arabinose, ribose, lyxose, glucose, mannose, galactose, maltose and lactose.

The method of the present invention makes it possible in particular to obtain, with excellent yield and selectivity, an aldonic acid from a 2-ketoaldonic acid of higher order.

The aldonic acids obtained by carrying out the method according to the invention are of great interest in themselves but are above all important intermediates in synthesis. In fact, a supplementary stage of hydrogenation makes it possible to easily obtain the corresponding alditols which are polyols which may be used in multiple applications, and in particular as non-cariogenic and low-calorie substitutes for saccharose.

These aldonic acids also constitute a raw material of interest for preparing biocompatible and/or biodegradable polymers which can be used in the food and medical fields.

It is while studying the already ancient method described in the patent JP 38.15610 of 1963 and taken up again by H. S. ISBELL et al. in the article of Carbohydrate research, 36, 1974, pages 283 to 291, which recommends the use of hydrogen peroxide on sodium salts of 2-ketoaldonic acids in a controlled reaction medium in order to obtain aldonic acids of lower order, that the Applicant company has developed this new method of manufacturing an acid derivative of ose.

This traditional method makes it possible to go, generally speaking, from the sodium salt of an aldonic acid with n+1 carbon atoms containing a ketone function in α, to an acid derivative of ose with n carbon atoms, thanks to the oxygenated water in a reaction medium where the pH is kept constant by the addition of soda or hydrochloric acid.

The conversion of the sodium salt of 2-ketogluconic acid into the sodium salt of arabinonic acid can thus be realised according to this method.

However, the selectivity of said reaction remains relatively low, for significant quantities of the salts of erythronic acid and formic acid are co-produced with those of arabinonic acid. Furthermore, the regulation of the pH of the reaction leads to a significant, equimolar even, consumption of soda.

During an in-depth investigation of this reaction, the Applicant company discovered that if the reaction is conducted without any pH regulation, one can, in an unexpected manner, remarkably improve the selectivity of the reaction.

Indeed, none of the documents of the prior art quoted above either describes or suggests the use of hydrogen peroxide without pH regulation for the oxidative decarboxylation of an acid derivative of ose containing at least one ketone function in α, or one of its salts.

Nothing in particular suggests that it is possible to increase considerably the selectivity of said reaction and thus the purity of the aldonic acid produced, which translates into a significant reduction of the production of co-products such as formic acid.

This new reaction thus has an important potential and there does not exist, to the knowledge of the applicant company, any equivalent reaction.

Thus, according to the invention, the method of manufacturing an acid derivative of ose containing n carbon atoms on the carbonic chain is characterised by the fact that an acid derivative of ose with n+1 carbon atoms containing at least one α ketone function, and/or one of its salts, is brought into contact with hydrogen peroxide in a reaction medium without pH regulation.

The method according to the invention thus makes use of an acid derivative of ose with n+1 carbon atoms containing at least one α ketone function, and/or one of its salts.

In the present invention, as indicated before, what is meant by acid derivative of ose with n+1 carbon atoms containing at least one α ketone function is a mono- or dicarboxylic acid derivative of an aldose having at least one ketone function in α position. This definition encompasses in particular:

the α-ketoaldonic acids, which are monocarboxylic acids derived from aldoses by replacing the aldehyde group by a carboxy group, and replacing the secondary hydroxyl function in α position by a ketone function, such as the α-ketogluconic, α-ketoglucoheptonic, α-ketomannonic, α-ketoidonic, α-ketogulonic, α-ketogalactonic, α-ketolyxonic, α-ketoxylonic, α-ketoarabinonic, α-ketoribonic, α-ketomaltobionic and α-ketolactobionic acids, of series D or L, and in particular the 2-keto-D-gluconic acid, the 2,5-diketo-D-gluconic acid and the 2-keto-L-gulonic acid, the α-ketoaldaric acids, which are dicarboxylic acids derived from aldoses by replacing the two terminal groups (CHO and $CH_2OH$) by carboxy groups and replacing at least one secondary hydroxyl function in α position by a ketone function, such as α-ketoglucaric, α-ketogalactaric, α-ketoarabinaric and α-ketoxylaric acids.

In the present invention, what is meant in particular by "salt of an acid derivative of ose" is a product chosen from the group comprising the alkaline and alkaline-earth salts of any acid derivative of ose such as defined before.

Thus, for example, the calcium and sodium salts of these acid derivatives of ose are perfectly suitable. These can be in particular calcium or sodium salts of 2-ketogluconic acid.

The acid derivatives of ose with n+1 carbon atoms containing at least one α ketone function are obtained in known fashion by oxidation of the oses or of the corresponding acid derivatives of ose. This oxidation stage can be carried out either by a chemical process or by a microbiological process.

Within the framework of the present invention, there is no particular constraint in terms of the dry matter of the reaction medium. In practice, the method according to the invention is characterised by the fact that the acid derivative of ose with n+1 carbon atoms and having at least one ketone function in α, or one of its salts, is provided in a quantity such that its concentration in the reaction medium is between 1 and 90% by weight, preferably between 10 and 50% by weight.

Only the constraints of minimum dry matter are imposed for obvious reasons of saving water evaporation and reducing the size of the reactors.

In the particular case of the calcium salt of the acid derivative of ose, it is recommended that too high an amount of dry matter be avoided. Indeed, it is known that the poor solubility of said calcium salt causes an increase in the viscosity of the reaction medium.

To the acid derivative of ose with n+1 carbon atoms containing at least one ketone function in α, or one of its salts, is slowly added, with stirring, the hydrogen peroxide, preferably in the form of oxygenated water of a strength of 20 to 70%, preferably of the order of 35%, as will be exemplified below.

In a preferred manner according to the invention, the oxygenated water is added in an at the most equimolar quantity in relation to the acid derivative of ose with n+1 carbon atoms having at least one ketone function in α.

Indeed, the Applicant company has not only shown that the decarboxylation reaction according to the invention does not require, contrary to what is recommended for the implementation of the method of prior art, the use of an excess of oxygenated water, but also that said excess of oxygenated water is responsible for the parasitic formation of formic acid and aldonic acids of lower order.

As has been mentioned above, a pH regulation is not carried out either, and the Applicant Company noticed in this connection, in a surprising and unexpected manner, that the selectivity of the reaction is distinctly improved.

For this reason, and this is what constitutes an important advantage of the method according to the invention, the reaction neither consumes nor generates salts.

In these conditions, it should be noted that no production of sodium chlorides or carbonates will be deplored during the reaction.

The method according to the invention is thus implemented without pH regulation, whatever the form of the acid derivative of ose introduced into the reaction medium.

The method of the invention is also implemented at a temperature of between 0 and 100° C., preferably between 20 and 90° C.

In the particular case where decarboxylation of the acid form of the acid derivative of ose with n+1 carbon atoms having at least one α ketone function is chosen, it is recommended that the reaction medium be heated since the reaction is slower.

However, implementing the decarboxylation of the salts of acid derivatives of ose is advantageously preferred. Indeed, this reaction being exothermic, it is advantageously recommended that this released energy be used to ensure the heating of the reaction medium.

This result thus constitutes another advantage of the method according to the invention, for no expenditure of energy external to the system is required, which then represents an appreciable economic benefit from the industrial point of view.

The regulation of the temperature is therefore not a limiting factor. One can thus proceed to start the reaction at ambient temperature, and when, by addition of oxygenated water, the temperature of the reaction medium reaches approximately 40° C., keep it at this level by cooling, by any means known per se.

However, it has been observed that this temperature regulation is not an absolute necessity, for neither the yield nor the selectivity is significantly affected by the uncontrolled rise in temperature of the reaction medium.

However, it is generally admitted that temperatures higher than 90° C., besides requiring the use of reactors resisting pressure, can lead to a degradation of the products of the reaction.

Isolating the products of the reaction is carried out by simple filtration, in the case where the calcium salt of the acid derivative of ose is chosen, for the latter has the advantage of precipitating naturally in the reaction medium, or by processing in the dark in order to bleach and eliminate the possible residual oxygenated water in the case where the sodium salt of the acid derivative of ose is chosen.

Finally, the reaction medium is advantageously concentrated by any means known per se, in order to encourage the spontaneous crystallisation of the product of the reaction.

The invention will be better understood by means of the examples which follow and which are intended solely to illustrate the invention better without wishing to reduce it to the embodiments expressly described and to the acid derivative of ose used.

EXAMPLE 1

1500 g of sodium 2-ketogluconate (6.94 moles) are dissolved in 3 l of water. The oxygenated water at 35% w/w (674 g, 6.94 moles) is added over 2 hours and with stirring.

The temperature of the reaction increases progressively by 1° C./min, and when it reaches 40° C., the reaction medium is cooled in order to keep it at this temperature.

The reaction is continued for 3 further hours, which corresponds to the time necessary for the concentration of peroxide to be less than 25 ppm.

A gaseous release of carbon dioxide is observed during the first hours of the reaction, and a check on the good progress of the reaction is carried out by measuring the level of reducing sugars by the Bertrand method, to a final value lower than 1% dry/dry.

After the reaction, the reaction medium is processed in the dark for 1 hour at 20° C., which makes it possible to bleach the reaction medium and to destroy the 10 to 25 ppm of residual peroxides.

After filtration, the solution is concentrated to a concentration of 600 g/l, the value at which arabinonate crystallises spontaneously.

The conversion rate is 100%, and the final yield of sodium arabinonate is 98%. No significant production of sodium salts of formic acid and erythronic acid is deplored.

EXAMPLE 2

1670 g of calcium 2-ketogluconate (3.47 moles, containing 11.6% water) are placed in solution in 3 l water. The oxygenated water at 35% w/w (674.5 g, 6.94 moles) is added in 2 hours with stirring. The temperature of the reaction increases progressively by 1° C./min and when it reaches 40° C., the reaction medium is cooled in order to keep it at this temperature.

The reaction is continued for 3 further hours, which corresponds to the time necessary for the concentration of peroxides to be lower than 25 ppm.

A gaseous release of carbon dioxide is observed during the first hours of the reaction.

The calcium 2-ketogluconate dissolving progressively in the course of the addition of oxygenated water, the medium then becomes limpid.

The calcium arabinonate precipitates when 80% of the oxygenated water has been introduced into the reaction medium. At this stage, good progress is checked by measuring the level of reducing sugars by the Bertrand method, to a final value lower than 1% on dry.

The reaction medium is then cooled to 20° C.

After filtration, the solid matter is dried. The conversion rate is 100%. The yield of calcium arabinonate after crystallisation is 93%. The product crystallises with 5 molecules of water. No significant production of sodium salts of formic acid and erythronic acid is deplored either.

EXAMPLE 3

The following tests 2 to 6 consist in preparing acid derivatives of ose as per the method according to the invention from salts of 2-ketogluconic acid, but modifying the operating conditions described in the previous Examples 1 and 2.

The products obtained at the end of the reaction have the characteristics set out in the table below and are compared with those prepared by the method of the prior art (Test no. 1).

| TESTS | 1 | 2 | 3 | 4 | 5 | 6 |
|---|---|---|---|---|---|---|
| Nature of the salt of the 2-ketogluconic acid | Sodium | Sodium | Calcium | Calcium | Calcium | Calcium |
| Quantities $H_2O_2$ (Equivalents) | 1.1 | 1 | 1.1 | 1 | 1.1 | 1 |
| Temperature (° C.) | 65–70 | 65–70 | 65–70 | 40 | 40 | 40 |
| pH adjusted to 7 | Yes | No | No | No | No | No |
| Dry matter (%) | 10 | 10 | 10 | 10 | 20 | 30 |
| Consumed soda (Equivalents) | 0.94 | 0 | 0 | 0 | 0 | 0 |
| Conversion rate (%) | 100 | 100 | 100 | 100 | 100 | 100 |
| Arabinonate salts (%*) | 91.4 | 98.5 | 97.5 | 99.3 | 98.3 | 99.3 |
| Erythronate salts (%*) | 2.5 | 0 | 0 | 0 | 0 | 0 |
| Formiate salts (%*) | 6.1 | 1.5 | 2.5 | 0.7 | 1.7 | 0.7 |

*molar yield

The results show clearly that the absence of pH regulation in the method according to the invention makes it possible to achieve a better selectivity of the reaction than that obtained with the method conducted in controlled conditions.

The production yields of arabinonate from 2-ketogluconate are, moreover, greater than 98.5% and this, whatever the temperature used, when the reaction is conducted without pH regulation and in introducing also an equimolar quantity of oxygenated water. Thus, no significant production of co-products of the reaction is deplored, and one can note the absence of formation of erythronic acid.

It is clearly apparent that the method according to the invention makes it possible to obtain arabinonate from 2-ketogluconate acid with a yield and selectivity never yet achieved.

EXAMPLE 4

In this case, one carries out a method identical to that described in Example 1, apart from the sodium 2-ketogluconate being replaced, weight for weight, by sodium 2-ketogulonate.

In these conditions, a conversion rate of 100% is also obtained. The yield of sodium xylonate is 98.5%.

What is claimed is:

1. Method of manufacturing an acid derivative of ose containing n carbon atoms on the carbonic chain, wherein an acid derivative of ose with n+1 carbon atoms, containing at least one a ketone function or one of its salts is brought into contact with hydrogen peroxide in a reaction medium without controlling the pH of the reaction medium.

2. The manufacturing method according to claim 1, wherein the acid derivative of ose containing at least one a ketone function or one of its salts is provided in a quantity such that its concentration in the reaction medium is between 1% and 90% by weight.

3. The manufacturing method according to claim 1, wherein hydrogen peroxide is used, optionally in the form of oxygenated water, of a strength of 20% to 70%.

4. The manufacturing method according to claim 1, wherein oxygenated water is introduced into the reaction medium in an at the most equimolar quantity in relation to said acid derivative of ose with n+1 carbon atoms containing at least one a ketone function.

5. The manufacturing method according to claim 1, wherein said method is conducted at a temperature of between 0° C. to 100° C.

6. The manufacturing method according to claim 1, wherein the acid derivative of ose with n+1 carbon atoms containing at least one a ketone function is chosen from the group consisting of the 2-keto-D-gluconic, 2,5-diketo-D-gluconic and 2-keto-L-gulonic acids and one of its calcium or sodium salts.

7. The manufacturing method according to claim 2, wherein hydrogen peroxide is used, optionally in the form of oxygenated water, of a strength of 20% to 70%.

8. The manufacturing method according to claim 2, wherein oxygenated water is introduced into the reaction medium in an at the most equimolar quantity in relation to said acid derivative of ose with n+1 carbon atoms containing at least one a ketone function.

9. The manufacturing method according to claim 3, wherein oxygenated water is introduced into the reaction medium in an at the most equimolar quantity in relation to said acid derivative of ose with n+1 carbon atoms containing at least one a ketone function.

10. The manufacturing method according to claim 2, wherein said method is conducted at a temperature of between 0° C. to 100° C.

11. The manufacturing method according to claim 3, wherein said method is conducted at a temperature of between 0° C. to 100° C.

12. The manufacturing method according to claim 4, wherein said method is conducted at a temperature of between 0° C. to 100° C.

13. The manufacturing method according to claim 2, wherein the acid derivative of ose with n+1 carbon atoms containing at least one a ketone function is chosen from the group consisting of the 2-keto-D-gluconic, 2,5-diketo-D-gluconic and 2-keto-L-gulonic acids and one of its calcium or sodium salts.

14. The manufacturing method according to claim 3, wherein the acid derivative of ose with n+1 carbon atoms containing at least one α ketone function is chosen from the group consisting of the 2-keto-D-gluconic, 2,5-diketo-D-gluconic and 2-keto-L-gulonic acids and one of its calcium or sodium salts.

15. The manufacturing method according to claim 4, wherein the acid derivative of ose with n+1 carbon atoms containing at least one a ketone function is chosen from the group consisting of the 2-keto-D-gluconic, 2,5-diketo-D-gluconic and 2-keto-L-gulonic acids and one of its calcium or sodium salts.

16. The manufacturing method according to claim 5, wherein the acid derivative of ose with n+1 carbon atoms containing at least one a ketone function is chosen from the group consisting of the 2-keto-D-gluconic, 2,5-diketo-D-gluconic and 2-keto-L-gulonic acids and one of its calcium or sodium salts.

17. The manufacturing method according to claim 2, wherein the acid derivative of ose containing at least one a ketone function or one of its salts is provided in a quantity such that its concentration in the reaction medium is between 10% and 50% by weight.

18. The manufacturing method according to claim 3, wherein hydrogen peroxide is used, optionally in the form of oxygenated water, of a strength of approximately 35%.

19. The manufacturing method according to claim 7, wherein hydrogen peroxide is used, optionally in the form of oxygenated water, of a strength of approximately 35%.

20. The manufacturing method according to claim 5, wherein said method is conducted at a temperature of between 10° C. to 90° C.

* * * * *